(12) United States Patent
Matsuno

(10) Patent No.: US 9,750,478 B2
(45) Date of Patent: Sep. 5, 2017

(54) X-RAY IMAGE PHOTOGRAPHING APPARATUS AND MANAGEMENT METHOD

(71) Applicant: Canon Kabushiki Kaisha, Tokyo (JP)

(72) Inventor: Hiroyuki Matsuno, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/730,392

(22) Filed: Jun. 4, 2015

(65) Prior Publication Data

US 2015/0265239 A1 Sep. 24, 2015

Related U.S. Application Data

(63) Continuation of application No. 14/079,511, filed on Nov. 13, 2013, which is a continuation of application No. 11/459,302, filed on Jul. 21, 2006, now abandoned.

(30) Foreign Application Priority Data

Aug. 10, 2005 (JP) .................................. 2005-232046

(51) Int. Cl.
| | |
|---|---|
| *H05G 1/44* | (2006.01) |
| *G06Q 10/00* | (2012.01) |
| *G06Q 50/00* | (2012.01) |
| *A61B 6/00* | (2006.01) |
| *G06F 19/00* | (2011.01) |

(52) U.S. Cl.
CPC ............... *A61B 6/563* (2013.01); *A61B 6/00* (2013.01); *A61B 6/465* (2013.01); *A61B 6/468* (2013.01); *A61B 6/469* (2013.01); *G06F 19/321* (2013.01)

(58) Field of Classification Search
USPC ........................................... 705/2–3; 378/108
See application file for complete search history.

(56) References Cited

U.S. PATENT DOCUMENTS

| | | | | |
|---|---|---|---|---|
| 5,513,101 | A * | 4/1996 | Pinsky | G06Q 50/24 705/3 |
| 6,282,513 | B1 * | 8/2001 | Strawder | G06Q 10/04 208/162 |
| 2003/0002629 | A1 * | 1/2003 | Takasawa | G06F 19/321 378/165 |

OTHER PUBLICATIONS

Dow Smith, et al., "Optical Image Evaluation and the Transfer Function", Applied Optics, Apr. 1963, vol. 2, No. 4, pp. 335-350.*

* cited by examiner

*Primary Examiner* — Amber A Misiaszek
(74) *Attorney, Agent, or Firm* — Canon USA Inc., IP Division

(57) ABSTRACT

When a retake button is selected, a CPU causes a dialog screen for inputting a reason for a photographic error to be displayed. On the dialog screen, the name of a radiographer who is logging onto an X-ray photographing apparatus and select buttons indicating possible reasons for photographic errors are indicated. The CPU transmits an unsatisfactorily photographed image to a different server.

14 Claims, 8 Drawing Sheets

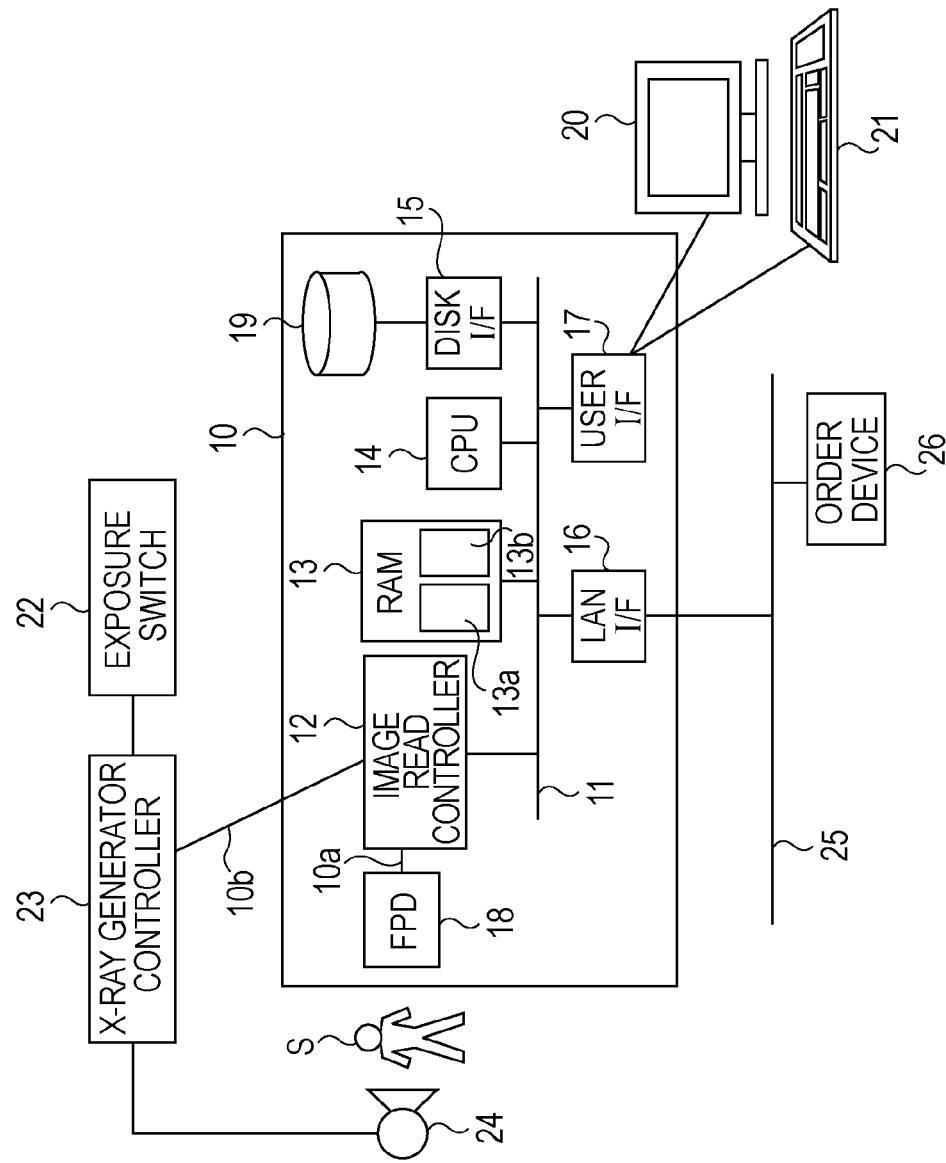

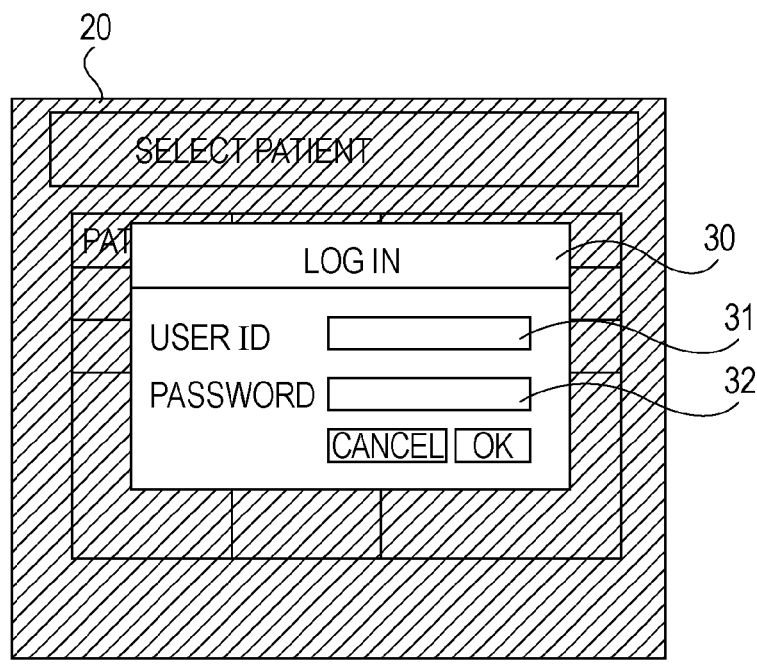

| # | PHOTOGRAPHED REGION | RADIOGRAPHER NAME | VALID | REASON FOR INVALIDATION |
|---|---|---|---|---|
| 1 | FRONT SIDE OF CHEST | TANAKA TAKESHI | ○ | — |
| 2 | OBLIQUE POSITION OF CHEST | TANAKA TAKESHI | × | MOTION |
| 3 | OBLIQUE POSITION OF CHEST | TANAKA TAKESHI | ○ | — |

X-RAY IMAGE PHOTOGRAPHING APPARATUS AND MANAGEMENT METHOD

CROSS-REFERENCE TO RELATED APPLICATIONS

This application is a Continuation of U.S. patent application Ser. No. 14/079,511 filed Nov. 13, 2013, which is a continuation of application Ser. No. 11/459,302 filed Jul. 21, 2006, now abandoned, which claims priority benefit of Japanese Application No. 2005-232046 filed Aug. 10, 2005. The disclosures of the above-named applications are hereby incorporated by reference herein in their entirety.

BACKGROUND OF THE INVENTION

Field of the Invention

The present invention relates to an X-ray image photographing apparatus and a management method in which images that are unsuccessfully X-ray photographed are treated as unsatisfactorily photographed images.

Description of the Related Art

Film-screen systems in which intensifying screens and X-ray photographic film are combined together have been widely used for X-ray photography in medical diagnosis. A photography order requested by a doctor is returned to the doctor as X-ray film, and the doctor observes the X-ray film on an X-ray film observation device. In this case, in order to observe a diagnosis region easily, a density range in which observation can be easily achieved, such as a contrast range of about 1.0 D to 1.5 D, is set. However, if a deviation from photographic conditions occurs, overexposure or underexposure is likely to occur. This adversely affects diagnosis. Thus, unsuccessfully photographed film is not used for diagnosis. Such failure film is disposed of as unsatisfactorily photographed film.

In recent years, such film-screen systems have been replaced with X-ray photographing systems that acquire image signals from photostimulable phosphors accumulating X-ray energy or flat-panel detectors (FPDs) that convert X-ray beams into electric signals proportional to the intensity of the X-ray beams.

Such photographing apparatuses solve an existing problem of exposure control. In particular, by using an FPD, a user is able to check an image immediately after the image is photographed. Thus, the user is able to determine, without waiting for film development or without waiting for reading processing of photostimulable phosphors, whether or not photography is successfully performed immediately after the photography is performed, and the user is able to quickly retake a photograph for a photography order for which photography has been unsuccessfully performed. Thus, the waiting period required for persons who are exposed to X-rays and radiographers is significantly reduced.

When a digital X-ray photographing apparatus is used, if a photographed image is not appropriate, outputting the image onto film wastes resources and money. Thus, a medical printer described in Japanese Patent Laid-Open No. 2001-175771 and a system that stops an unsatisfactorily photographed image being distributed to an image server used for diagnosis are proposed.

In this case, preventing an unsatisfactorily photographed image from being transmitted to the image server is effective in reducing the load of a network and in reducing the amount of image server capacity used.

In known film-screen systems, a manager, such as a head radiographer or a chief radiographer, checks unsatisfactorily photographed film. Thus, the manager is able to check the number of unsatisfactorily photographed images from among a plurality of photographed images and the type of error a radiographer repeatedly makes, and thus, is able to supervise X-ray photography. In such a situation, radiographers carefully perform photography under strict supervision.

Using the digital X-ray photographing apparatus reduces the cost relating to unsatisfactorily photographed film, and this reduction in the cost contributes to hospital management. However, management of unsatisfactorily photographed images is not performed properly, and the number of unsatisfactorily photographed images is unclear. Thus, unsatisfactorily photographed images can be generated easily. That is, a subject is likely to be unnecessarily exposed to radiation, and such unnecessary exposure is detrimental to patient's health.

SUMMARY OF THE INVENTION

The present invention can transmit an unsatisfactorily photographed image or photography information to an X-ray photography management server apparatus in order to manage a photography record including the skill of a radiographer and a photographic error. Accordingly, an X-ray image photographing apparatus that performs digital photography and that achieves improved operation, and a management method are provided.

According to an aspect of the present invention, an X-ray image photographing apparatus including an image management system for handling and tracking data to be correlated with an unsatisfactorily photographed image, is provided which includes a photographic error indicating unit configured to mark or flag an image that is unsuccessfully photographed as an unsatisfactorily photographed image; an input unit configured to facilitate the inputting a reason for a photographic error; and a transmitting unit configured to transmit the unsatisfactorily photographed image and the reason for the photographic error.

According to another aspect of the present invention, the X-ray image photographing apparatus may further include a user managing unit configured to identify an operator who makes the photographic error, wherein the transmitting unit transmits user identification information as well as the unsatisfactorily photographed image and the reason for the photographic error. According to another aspect of the present invention, the x-ray image photographing apparatus may further include a compressing unit configured to compress the unsatisfactorily photographed image, which is indicated as being invalid, wherein the transmitting unit transmits the compressed image.

According to yet another aspect of the present invention, the transmitting unit transmits the unsatisfactorily photographed image and the reason for the photographic error at a predetermined point in time or at predetermined intervals. According to another aspect of the present invention, the transmitting unit transmits the unsatisfactorily photographed image, which is indicated as being invalid, and a valid image that is not indicated as being invalid to different servers.

Moreover, according to yet another aspect of the present invention, the X-ray image photographing apparatus may further include an X-ray generator configured to irradiate an X-ray; and a user managing unit for identifying an operator who makes the photographic error, wherein the transmitting unit transmits a photographic condition for the X-ray generator and user identification information as well as the unsatisfactorily photographed image and the reason for the photographic error. Further, according to yet another aspect of the present invention, the transmitting unit utilizes simple mail transfer protocol as a protocol for transmission.

According to still yet another aspect of the present invention, an image management method is provided which may be performed in an X-ray imaging apparatus including an image management system for handling and tracking data to be correlated with an unsatisfactorily photographed image. Here, the method includes marking/flagging an image that is unsuccessfully photographed as an unsatisfactorily photographed image; inputting a reason for a photographic error; and transmitting the unsatisfactorily photographed image and the reason for the photographic error.

Additionally, according to yet another aspect of the present invention, a computer readable medium is provided which contains computer-executable instructions to be executed in an X-ray imaging apparatus including an image management system for handling and tracking data to be correlated with an unsatisfactorily photographed image. The medium includes computer-executable instructions for marking/flagging an image that is unsuccessfully photographed as an unsatisfactorily photographed image; computer-executable instructions for inputting a reason for a photographic error; and computer-executable instructions for transmitting the unsatisfactorily photographed image and the reason for the photographic error.

Other embodiments, features and aspects of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate various embodiments, features and aspects of the present invention, and together with the description, serve to explain the principles of the invention.

FIG. 1 is a block circuit diagram of an exemplary X-ray image photographing apparatus, according to an aspect of the present invention.

FIG. 2 is a front view of an exemplary login screen for identifying an operator, according to an aspect of the present invention.

FIG. 3 is a front view of an exemplary screen on which a list of photography orders acquired by the X-ray photographing apparatus is displayed, according to an aspect of the present invention.

DESCRIPTION OF THE EMBODIMENTS

Figure 4:
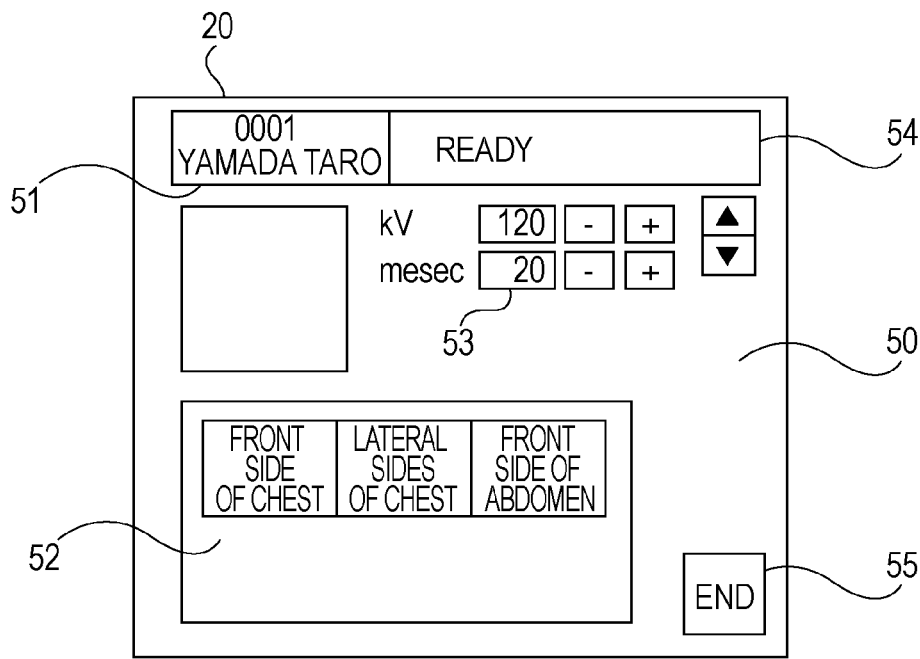
FIG. 4 is a front view of an exemplary screen on which photography order information received by the X-ray photographing apparatus is displayed, according to an aspect of the present invention.

Various embodiments, features and aspects of the present invention will now be herein described in detail in accordance with the accompanying drawings.

FIG. 1 is a block circuit diagram showing an exemplary system structure of a medical digital X-ray photographing apparatus according to an embodiment of the present invention. An X-ray photographing apparatus 10 includes an image read controller 12, a random-access memory (RAM) 13, a central processing unit (CPU) 14, a disk interface 15, a local-area network (LAN) interface 16, and a user interface 17 that are connected to each other via an internal bus 11. The RAM 13 includes a RAM unit 13a that stores a control program and a RAM unit 13b that temporarily stores images.

An output of a flat-panel detector (FPD) 18 that includes a phosphor and a large-screen photoelectric converter, is connected via a data line 10a, to the image read controller 12 that stores images. A hard disk 19 that stores a control program, correction information necessary for photography, and photographed images is connected to the disk interface 15. A display device 20 and an operation unit 21, such as a keyboard or a mouse, are connected to the user interface 17. It is noted that the display device 20 and the operation unit 21 may be replaced with a touch panel, or the like.

An output of an exposure switch 22 is connected, via an X-ray generator controller 23, to an X-ray tube 24. The X-ray tube 24 irradiates a person who is located in front of the FPD 18 with X-ray beams. The X-ray generator controller 23 is connected, via a synchronous signal line 10b, to the image read controller 12. An order device 26 is connected, via a LAN cable 25, to the LAN interface 16 used for communication with an external device.

The X-ray photographing apparatus 10 reads a control program from the hard disk 19, and causes the CPU 14 to operate the control program on the RAM unit 13a. In order to use the X-ray photographing apparatus 10, a radiographer logs in using the operation unit 21. Login management is performed, for example, for the purpose of management of skills of radiographers. It is necessary to specify the time an error occurs, the person who makes the error, and the reason the error occurred, in order to manage radiographers.

FIG. 2 is a front view of an exemplary login screen for identifying an operator, according to an aspect of the present invention. In order to avoid deception, in which a radiographer performs photography to cover for another radiographer, a user name and a password are input to a user ID input field 31 and a password input field 32, respectively, on the login screen 30 of the display device 20 shown in FIG. 2.

When user authentication is satisfactorily achieved and the login operation is completed, the CPU 14 receives from the order device 26 connected to the LAN cable 25 photography order information sent from a radiology information system (RIS), which is not shown in FIG. 1.

FIG. 3 is a front view of an exemplary screen on which a list of photography orders acquired by the X-ray photographing apparatus is displayed, according to an aspect of the present invention. In this embodiment, a list of the received photography order information is displayed, via the user interface 17, on a screen 40 of the display device 20, as shown in FIG. 3. The radiographer, who is the operator of the X-ray photographing apparatus 10, selects an inspection item 41 on the screen 40 using a pointing device.

FIG. 4 is a front view of an exemplary screen on which photography order information received by the X-ray photographing apparatus is displayed, according to an aspect of the present invention. Thus, for example, as shown in FIG. 4, the control program on the RAM unit 13a executed by the CPU 14 changes the screen 40 into a screen 50, and the received photography order information is displayed on the screen 50.

The CPU 14 presents to the operator the selected inspection item 41 in FIG. 3. Thus, during inspection, for example, a name is indicated in a subject information field 51 on the screen 50. A photographic condition indication field 53 that indicates photography items for a photography region indicated in a photography region field 52 as buttons, a system state indication field 54 that indicates a system state of the X-ray photographing apparatus 10, and an end button 55 are provided on the screen 50.

The CPU 14 executes the system control program. When the operator clicks a "front side of chest" button, which is the first photography order information indicated in the photography region field 52, the CPU 14 sets the "front side of chest" button so that the "front side of chest" button has been selected. The operator places a subject S between the FPD 18 and the X-ray tube 24, and adjusts the attitude (position) of the subject S to be appropriate for the photography region indicated in the photography region field 52. In the meantime, the CPU 14 performs controlling applying a voltage to the FPD 18 by executing the control program, and sets the FPD 18 to be in an X-ray photography enable state. When the CPU 14 detects that the FPD 18 is in the X-ray photography enable state, a message "READY" is indicated in the system state indication field 54.

The operator checks the screen of the system state indication field 54, and then, clicks the exposure switch 22 to input to the system a trigger for generating an X-ray beam. The generated exposure signal is input to the image read controller 12 via the X-ray generator controller 23 and the synchronous signal line 10b. The image read controller 12 confirms, via the data line 10a, that the FPD 18 is in the photography enable state, and then, the image read controller 12 generates an exposure enable signal. The exposure enable signal is returned to the X-ray generator controller 23. The X-ray generator controller 23 causes the X-ray tube 24 to irradiate an X-ray beam.

After irradiation of the X-ray beam, the X-ray beam passing through the subject S is acquired as digital data at the FPD 18 via a phosphor, which is not shown. Then, the digital data is transferred to the image read controller 12. Then, the CPU 14 executes the control program and controls the display device 20 via the user interface 17 so that a screen 60 is displayed on the display device 20, as shown in FIG. 5.

Figure 5:
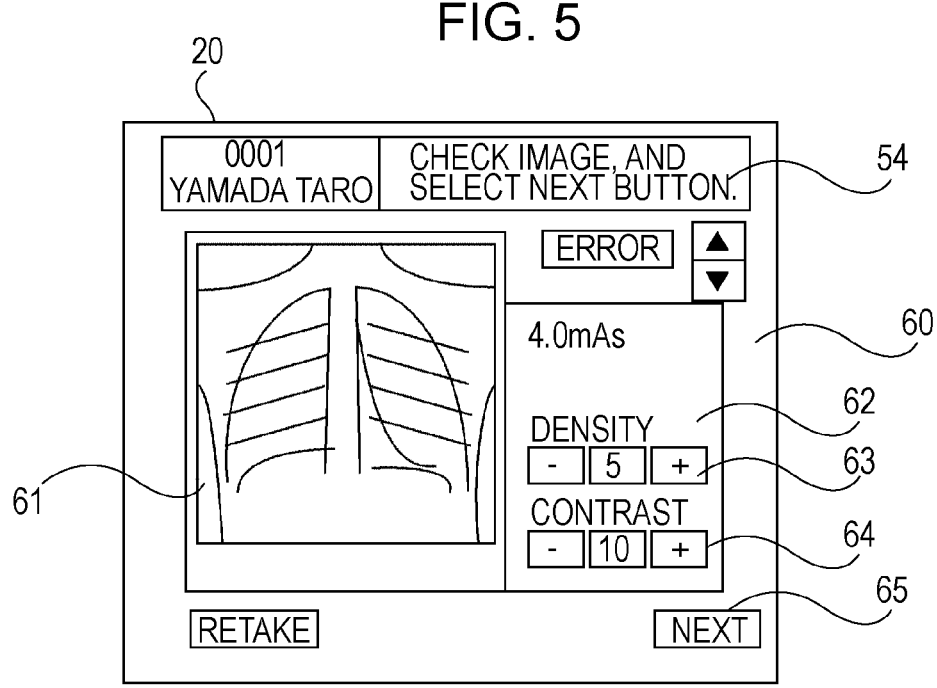
FIG. 5 is a front view of an exemplary screen of a display device after photography is performed, according to an aspect of the present invention.

FIG. 5 is a front view of an exemplary screen of a display device after photography is performed, according to an aspect of the present invention. The CPU 14 controls the display device 20 so that the image data acquired from the image read controller 12 is displayed in an image indication field 61 on the screen 60, and so that a dose value received as photography execution information from the X-ray generator controller 23 is indicated in a dose value indication field 62, and stores the image data and the photography execution information in the hard disk 19. In order to change an automatic density adjustment value for an image displayed in the image indication field 61, the operator changes the density of the photographed image by adjusting a density adjustment parameter 63. Similarly, the operator is able to change the contrast of the photographed image by adjusting a contrast adjustment parameter 64.

After checking the photographed image displayed in the image indication field 61 on the screen 60, the operator clicks a next button 65 on the screen in order to perform the next photography. The CPU 14 executes the program and controls the display device 20 so that the screen 50 shown in FIG. 4 is displayed again on the display device 20. The CPU 14 detects selection for the next order in the photography region field 52 by the operator via the user interface 17. The CPU 14 repeats a photography flow that is similar to the photography flow in the case described above until all the photography orders are dealt with.

When all the orders have been dealt with, the screen 60 is displayed again on the display device 20. Since there is no photography order to be dealt with, the CPU 14 changes the display of the next button 65 to a display of a message "end inspection". When the operator clicks the message "end inspection", the inspection of the subject S is terminated.

When termination of the inspection is directed, the control program transmits to the order device 26 the photographic conditions and the photography execution information stored in the hard disk 19. The CPU 14 reports to the order device 26, in accordance with a predetermined communication protocol, that photography has been terminated. At this time, the CPU 14 reports the photographic conditions under which photography has been performed and the photography execution information, such as an exposure dose, to the order device 26.

A photographed image is output to an external apparatus or the like as image data including additional information, such as the above-described photographic conditions and photography execution information, in accordance with a medical standard communication protocol called Digital Imaging Communication in Medicine (DICOM).

Figure 6:
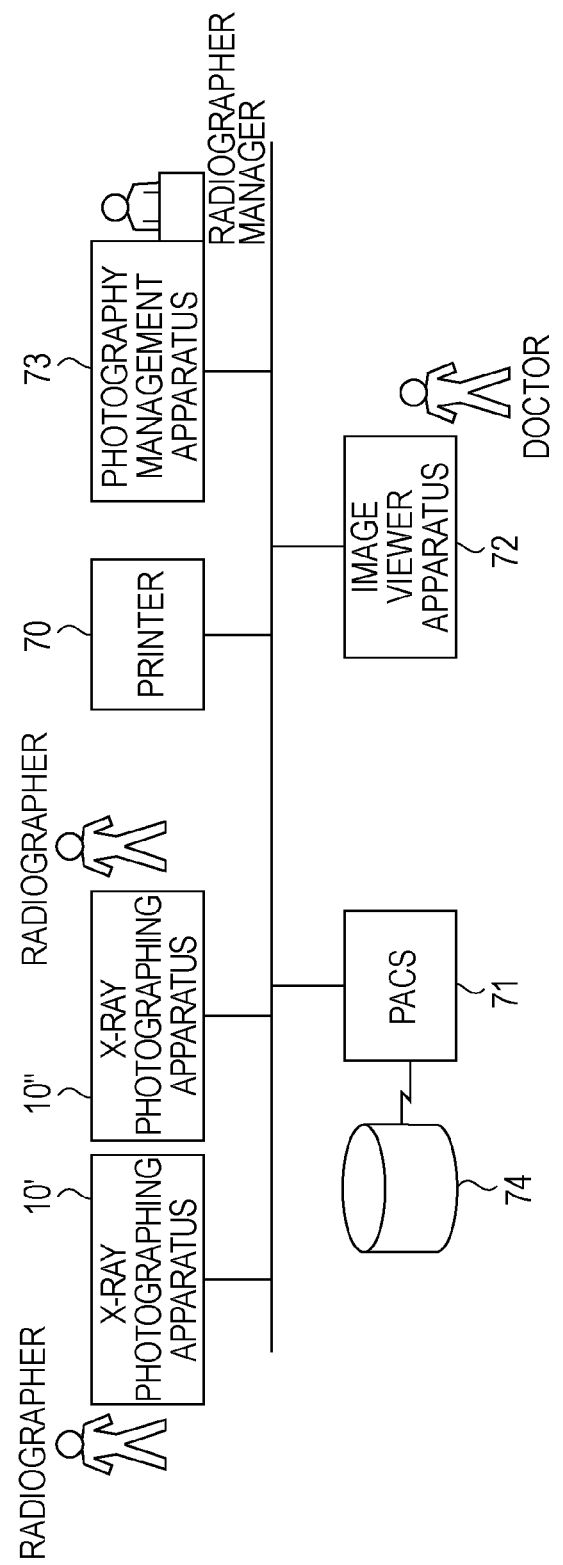
FIG. 6 is a block circuit diagram for explaining an exemplary embodiment, according to an aspect of the present invention.

FIG. 6 is a block circuit diagram for explaining an exemplary embodiment, according to an aspect of the present invention. For example, as shown in FIG. 6, a printer 70, a picture achieving and communication system (PACS) 71, an image viewer apparatus 72, and a photography management apparatus 73 are connected to X-ray photographing apparatuses 10' and 10". An external storage device 74 is connected via the PACS 71.

A doctor who gives a photography order carries out diagnosis using output film or an image displayed on the image viewer apparatus 72. After deciding diagnosis using the image viewer apparatus 72, the doctor creates a diagnostic report. After diagnostic report is stored into the PACS 71, the PACS 71 stores the image into the external storage device 74, and reports completion of storage to the X-ray photographing apparatuses 10' and 10". Each of the X-ray photographing apparatuses 10' and 10" receives the report about the completion of storage, and transmits photography execution record information to the photography management apparatus 73.

Although a method for photographing an image in accordance with request information has been described, a purpose of an inspection is to acquire an image of a photography region designated by a doctor. However, photography may not be successfully performed by a single operation. In many cases, photography is performed unsuccessfully due to blurring of an image caused by movement of a subject S. Due to failure in positioning, a so-called "unsatisfactorily photographed image", which is inappropriate and cannot be used for diagnosis, is generated.

In this case, the operator again photographs an image that has not been photographed successfully. For photography execution information to be returned to the RIS and an image to be used for diagnosis by the doctor, an unsatisfactorily photographed image acquired before retaking a photograph is not necessary. Only an image acquired by properly photographing a designated region under designated photographic conditions is necessary. However, images may be played back until diagnosis is completed even after photography is performed. Thus, not only photographed images, but also unsatisfactorily photographed images must be stored.

Figure 7:
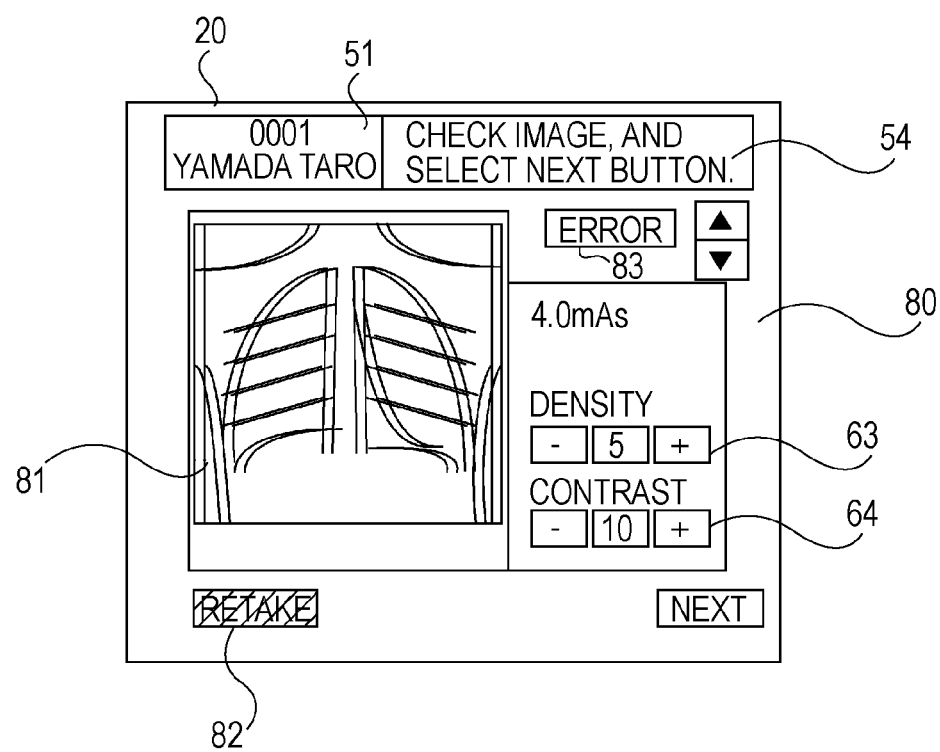
FIG. 7 is a front view of an exemplary screen when an unsatisfactorily photographed image is generated, according to an aspect of the present invention.

FIG. 7 is a front view of an exemplary screen when an unsatisfactorily photographed image is generated, according to an aspect of the present invention. An example in which a photographed image 81 is blurred and a photograph must be retaken since the subject S moves when being photographed is shown on a screen 80 in FIG. 7. When the operator determines that a photograph should be retaken and selects a retake button 82, the CPU 14 executes the control program to display a dialog screen 90 onto which the reason for invalidation, that is, the reason for the photographic error, is input, as shown in FIG. 8.

Figures 8, 9:
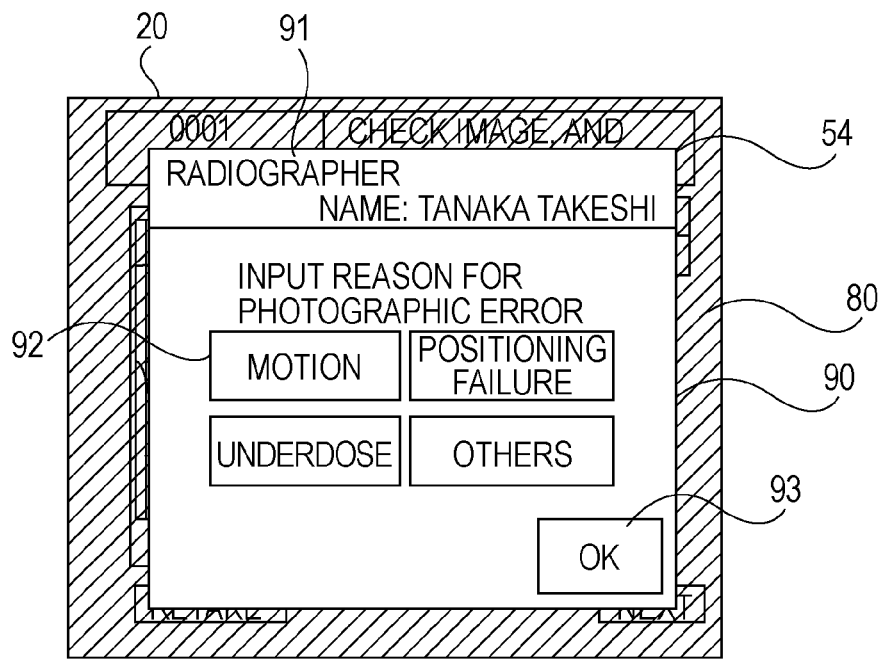
FIG. 8 is a front view of an exemplary screen for inputting a reason for retake or a photographic error, according to an aspect of the present invention.
FIG. 9 is an explanatory diagram showing an example of storage of photography records, according to an aspect of the present invention.

FIG. 8 is a front view of an exemplary screen for inputting a reason for retake or a photographic error, according to an aspect of the present invention. A radiographer name 91 who is logging onto the X-ray photographing apparatus and select buttons 92 indicating possible reasons for photographic errors are indicated on the screen 90. After the operator selects a reason for a photographic error and clicks an OK button 93 to fix the selection, the dialog screen 90 is closed. The CPU 14 stores the fixed data into a memory or a database, as shown in FIG. 9, and continues photography. Then, the CPU 14 controls the display device 20 so that the screen 50 is displayed on the display device 20, as shown in FIG. 4. The CPU 14 sets photography parameters to achieve the same conditions, and controls the FPD 18 so as to be the photography enable state.

In this case, generally, the same photographic conditions are set. However, the operator may change the conditions set in the photographic condition indication field 53 on the screen 50. After that, the operator clicks the exposure switch 22 to retake an image. Then, the retaken image is displayed, as shown in FIG. 5.

FIG. 9 is an explanatory diagram showing an example of storage of photography records, according to an aspect of the present invention. After the retaken image is displayed, as shown in FIG. 5, the photography record information 100 is stored in the memory, as shown in FIG. 9.

When the operator clicks an error button 83 (see FIG. 7), instead of the retake button 82, after photography is performed, the CPU 14 controls the display device 20 so that the dialog screen 90 is displayed, as shown in FIG. 8, and urges the operator to input the reason for the photographic error.

If operators transmit invalid images from the X-ray photographing apparatuses 10' and 10" to an external apparatus after completing photography for all the photography orders, film is wasted, and a large amount of capacity of the external storage device 74, which is connected to the PACS 71, is used. This interrupts image diagnosis performed by the doctor. Thus, by transmitting only a valid image to the printer 70 and the PACS 71 set in advance, the doctor who gives a photography order is able to receive only data necessary for diagnosis. Accordingly, a suitable system can be established.

However, with the arrangement described above, an unsatisfactorily photographed image and a reason for a photographic error remain within the X-ray photographing apparatus 10. Thus, the fact that a photograph is retaken and that a photographic error occurs is not reported to a radiographer manager. In addition, even if the subject S is irradiated with X-rays, images not transmitted to the PACS 71, which is a first server unit, are deleted from the oldest one when the hard disk 19 of the X-ray photographing apparatus 10 is full. That is, an unsatisfactorily photographed image is automatically deleted after a predetermined period passes unless the manager operates a plurality of X-ray photographing apparatuses and checks unsatisfactorily photographed images.

Thus, the control program executed by the CPU 14 of the X-ray photographing apparatus 10' in this embodiment transmits images #1 and #3 shown in FIG. 9 to the PACS 71, which is the first server unit, for diagnosis. In addition, the CPU 14 transmits photography information on images #1, #2, and #3 and an unsatisfactorily photographed image #2 to the photography management apparatus 73, which is a second sever unit, for a photography record.

When the photography management apparatus 73, which is the second photography management server unit, is configured to receive all the photography records on all the photography, that is, successfully performed photography for inspection requests and unsuccessfully performed photography, which generates a photographic error, from a client apparatus, X-ray photography records can be created. In addition, since an unsatisfactorily photographed image is also received, the consistency of the reason for the photographic error can be achieved by comparing the reason for the photographic error with the unsatisfactorily photographed image. If such a photography record is stored in a database to perform analysis for each radiographer, the manager is able to check the skill of the radiographer who is the operator of the X-ray photographing apparatus 10.

The X-ray photographing apparatus 10' may transmit photographic error information at a predetermined time when an inspection is terminated or when a photographed image is transmitted to an external apparatus. Alternatively, the X-ray photographing apparatus 10' may transmit the photographic error information every day or at a time when the X-ray photographing apparatus 10' receives a report indicating that storage into the printer 70 and the PACS 71 is completed or may transmit the photographic error information in association with accounting information of a hospital. In addition, in some cases, corrected photographed data is re-transmitted from the X-ray photographing apparatus 10' to an external apparatus for the reason that image processing is not properly performed, and the re-transmitted photographed data is used for diagnosis. However, needless to say, in such a case, photographic error information may not be re-transmitted to the photography management apparatus 73, which may serve/act as a second server unit.

In addition, the number of retransmission times may be managed. Even when the operator of the X-ray photographing apparatus 10 performs an operation that is different from a normal workflow, the operation is traced back, and transmitted to the photography management apparatus 73. Thus, the manager is able to check unsatisfactorily photographed images generated by the X-ray photographing apparatuses 10' and 10" and reasons for the photographic errors by operating a terminal on the photography management apparatus 73.

An aspect of the system according to this embodiment is to manage X-ray photography records. Thus, only all the photography records including photographic errors may be transferred between the X-ray photographing apparatus 10' and the photography management apparatus 73. In a case where unsatisfactorily photographed images are transferred, photographed images may be included. However, since the manager does not necessarily need a fine original image, the system may be configured to receive a reduced image created from an original image or an image subjected to image processing, such as lossy compression, so that the manager can confirm that the reason for the photographic error is proper.

In addition, since checked images can be automatically deleted, image protection flags attached to the checked images are deleted. A photography record received for each inspection is stored as a database on a computer serving as a server device. Thus, an X-ray photography management system can be configured to collect statistics for each radiographer or for each reason for photographic error. Under such control, an object to manage skills of radiographers while reducing the load of the server device can be satisfactorily achieved.

Figure 10:
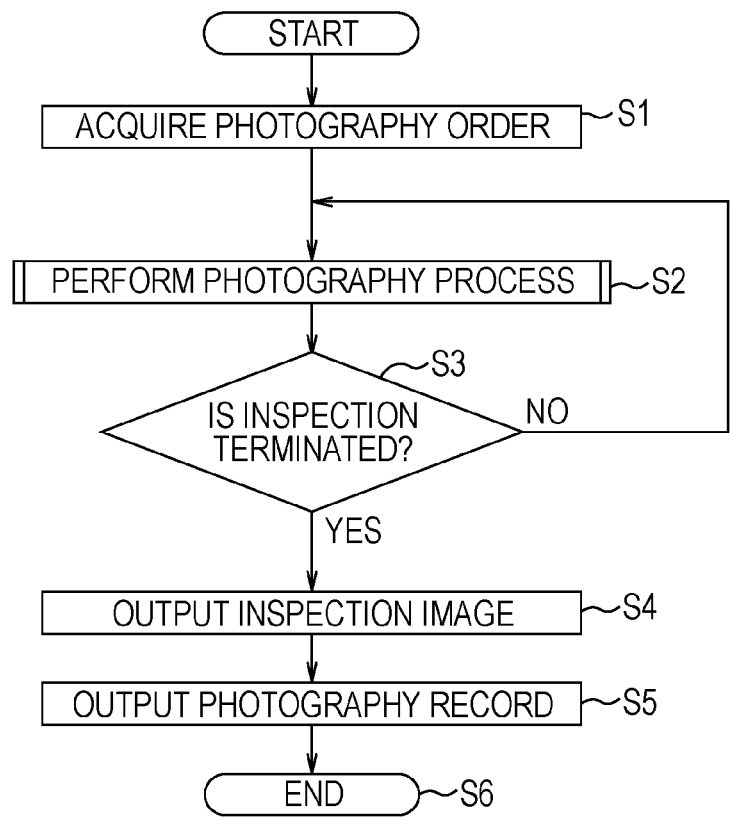
FIG. 10 is a flowchart of an exemplary output operation of an inspection image and a photography record, according to an aspect of the present invention.

FIG. 10 is a flowchart of an exemplary process of the control program executed by an X-ray photographing apparatus. When inspection starts, the control program acquires a photography order in step S1. Then, in step S2, a photography process is performed. In step S3, it is determined whether or not all the photography orders have been dealt with. If it is determined in step S3 that all the photography orders have not been dealt with (NO in step S3), the process returns to step S2 to perform the photography process. If it is determined in step S3 that all the photography orders have been dealt with (YES in step S3), the process proceeds to step S4. In step S4, only a valid inspection image is output to the PACS 71, which is the first server unit. A photographed image is transmitted using a protocol called DICOM, which is the communication standard of medical instruments.

Then, in step S5, some or all of the photography records are output to the photography management apparatus 73, which acts/functions as a second server unit. The photography records may be transmitted, for example, as photography execution information based on DICOM. However, in this embodiment, the photography execution information is transmitted using a Simple Mail Transfer Protocol (SMTP) used for transmitting electronic mail. In order to avoid electric interception or spoofing of the protocol, it is desirable that encrypted Secure Multipurpose Mail Exchange (S/MIME) be used.

In addition, an invalid image, which is unsatisfactorily photographed, is, for example, JPEG-compressed, and output together with the photography records. After completing the processing of the above-described steps, the program processing relating to the inspection request is terminated. Then, the process ends at step S6, and waits for execution for the subsequent photography order.

Figure 11:
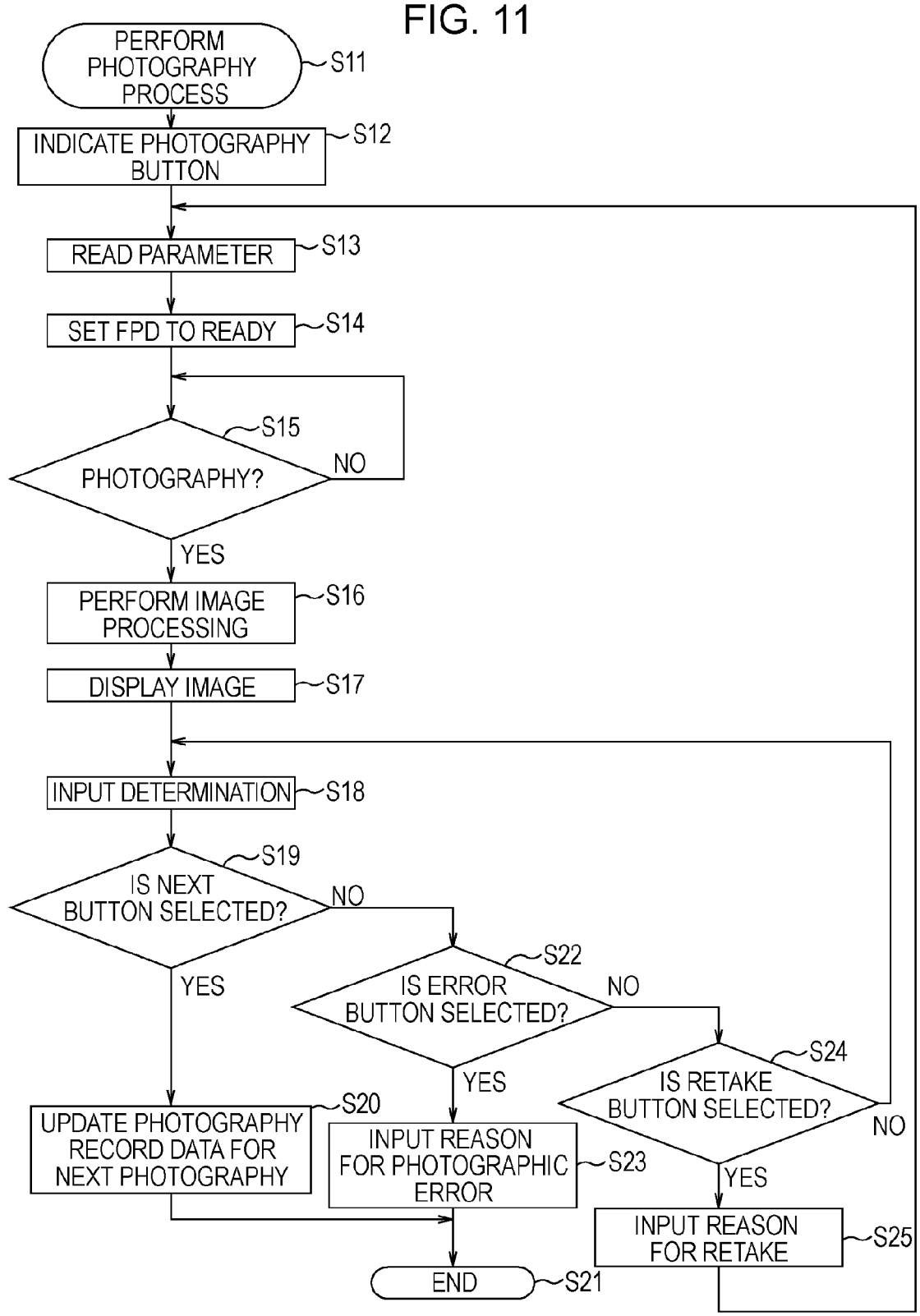
FIG. 11 is a flowchart of an exemplary photography process, according to an aspect of the present invention.

FIG. 11 is a flowchart of an exemplary photography process in step S2 shown in FIG. 10. In step S11, the photography process starts. In step S12, a "photography" button for a photography order to be dealt with is indicated. In step S13, a parameter corresponding to the photography order is read from the database. In step S14, the FPD 18, which is a sensor, is set the "READY" state, and is held in the "READY" state until X-ray photography is performed in step S15. When photography is performed, image analysis is performed in step S16. Then, an image is displayed on the display device 20 in step S17.

When an operator changes an image processing parameter while viewing an image, an image processing parameter adjustment screen is displayed. After the operator changes the image processing parameter, the changed parameter is fixed. When an image processing parameter is not changed, determination of whether or not the photographed image is usable for diagnosis is input in step S18. If it is determined in step S19 that a "next" button is selected (YES in step S19), photography record data is updated in order to perform the next photography in step S20. Then, in step S21, the photography process ends.

If it is determined in step S19 that the "next" button is not selected (NO in step S22), it is determined in step S22 whether or not an "error" button is selected. If it is determined in step S22 that the "error" button is selected (YES in step S23), a reason for the photographic error is input, as described above, and the photography record is written as a photographic error in step S23. Then, the photography process ends in step S21.

If it is determined in step S22 that the "error" button is not selected (NO in step S22), it is determined in step S24 whether or not a "retake" button is selected. If it is determined in step S24 that the "retake" button is selected (YES in step S24), the process proceeds to step S25. In step S25, a reason for retaking a photograph is input, as described above, in order to add and indicate a photographic error mark indicating that the image is invalid and needs to be retaken, and the photography record data is updated. Then, the process returns to step S13, and X-ray photography waiting processing is performed. If it is determined in step S24 that the "retake" button is not selected (NO in step S24), the process returns to step S18 to perform determination of photography again.

In this embodiment, a case where the control program is stored in the hard disk 19, transferred to the RAM 13, and executed by the CPU 14 has been explained. However, implementation of the control program is not necessarily limited to this case. The control program may be implemented using any storage medium. In addition, the control program may be implemented using a circuit that performs a similar operation.

The foregoing embodiments may be applied to a system including a plurality of apparatuses or may be applied to an apparatus formed by a single device. For example, the foregoing embodiments may be achieved by supplying a recording medium on which program code of software for realizing the functions of the foregoing embodiments is recorded to a system or an apparatus and by reading and executing the stored program code by a computer or a CPU. In this case, the program code itself read from the recording medium attains the functions of the foregoing embodiments, and the recording medium recoding the program code constitutes the present invention.

The recording medium for supplying the program code may be, for example, a floppy disk, a hard disk, an optical disk, a magneto-optical disk, a compact disc read-only memory (CD-ROM), a compact disc-recordable (CD-R), a magnetic tape, a nonvolatile memory card, a ROM, or the like.

In addition, the functions of the foregoing embodiments can be attained not only by executing the read program code by the computer but also by performing part or all of the actual processing by an OS or the like running on the computer on the basis of instructions of the program code.

Furthermore, the program code read from the recording medium is written to a memory arranged in a function expansion board of the computer or a function expansion unit connected to the computer and is used. The functions of the foregoing embodiments can also be attained by performing part or all of the actual processing by the CPU or the like arranged in the function expansion board or the function expansion unit on the basis of instructions of the program code.

The program of the program code of the software for realizing the functions of the foregoing embodiments may be distributed to a requester from the recording medium recording the program code via a communication line, such as the Internet.

In the foregoing embodiments, an example in which a plurality of operators operates an X-ray photographing apparatus and in which each of the operators inputs a user name and a password for identification has been explained. However, if biometrics, such as fingerprint or iris recognition, is adopted, a system with higher security and higher operability can be established. In addition, when an operator uses an X-ray photographing apparatus, a nameplate used in the hospital including a barcode or an IC tag may be used for authentication of the operator. In any cases, an operator of an X-ray photographing apparatus is identified, and a photography record is transmitted to a management apparatus.

In addition, since an X-ray photography management server unit is a program executed by the CPU 14, the program is not necessarily executed on the photography management apparatus 73. For example, the X-ray photographing management server unit may be configured within the X-ray photographing apparatus 10'. In this case, the X-ray photography management function can be realized when a manager uses the X-ray photographing apparatus 10'.

In addition, if a single operator uses an X-ray photographing apparatus in a small hospital or the like, a login step is not necessary since identification of the operator is not required. Thus, display of the login screen shown in FIG. 2 can be omitted by using a predetermined user name. In this case, the X-ray photography apparatus itself is capable of implementing the X-ray photography management function by arranging the X-ray photography management server unit within the X-ray photography apparatus.

The present invention is not necessarily limited to the foregoing embodiments. Various changes and modifications can be made to the present invention without departing from the scope of the gist of the present invention.

As described above, in an X-ray image photographing apparatus, a management system, and a management method according to embodiments of the present invention, a photography management server apparatus operated by a manager receives an occurrence record of a photographic error and an unsatisfactorily photographed image, which are not delivered for diagnosis, from a client apparatus. Thus, an X-ray photography management system that is capable of referring to a digital unsatisfactorily photographed image, which replaces known unsatisfactorily photographed film, can be realized. In addition, since an X-ray photography management system that is capable of collecting statistics on photographic errors for each radiographer can be realized, implementation of such an X-ray photography management system contributes to hospital management in terms of patient protection.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

The invention claimed is:

1. A control apparatus for medical imaging, comprising:
a control unit configured to control a medical imaging unit for detecting an X-ray to obtain a medical image; and
a communication unit configured to transmit the obtained medical image to an external apparatus,
wherein the control unit is configured to associate error information with the obtained medical image, wherein the error information indicates an error in the medical imaging for the obtained medical image,
wherein, in a case where the control unit associates the error information with the obtained medical image, the communication unit is configured to transmit the obtained medical image to a first external apparatus which is independent from the control apparatus and is configured to store the obtained medical image associated with the error information, and
wherein, in a case where the control unit does not associate the error information with the obtained medical image, the communication unit is configured to transmit the obtained medical image to a second external apparatus which is independent from the control apparatus and different from the first external apparatus and is configured to store the obtained image to be used for diagnosis.

2. The control apparatus of claim 1, wherein
the communication unit is configured to transmit the obtained medical image with which the error information is associated, to the first external apparatus, and to transmit the obtained medical image with which the error information is not associated, to the second external apparatus.

3. The control apparatus of claim 2, wherein
the first external apparatus is independent from the second external apparatus.

4. The control apparatus of claim 1, wherein
the communication unit is configured to transmit the obtained medical image based on a DICOM protocol.

5. The control apparatus of claim 1, wherein
the communication unit is configured to transmit an image obtained by lossy compression of the obtained medical image.

6. The control apparatus of claim 1, wherein
the communication unit is configured to transmit the obtained medical image with which the error information is associated, and the error information, to the first external apparatus.

7. The control apparatus of claim 1, wherein the control unit is configured to obtain medical images from the medical imaging unit, and
wherein, in a case where the control unit associates one of the obtained medical images with the error information, the communication unit is configured to transmit the one of the medical images associated with the error information to the first external apparatus, and to transmit the medical images not associated with the error information to the second external apparatus.

8. The control apparatus of claim 1, wherein
the communication unit is configured to, in a case where the control unit associate the error information with a first medical image from the medical imaging unit, and a second medical image is received from the medical imaging unit, transmit an image based on the first medical image associated with the error information, and an image based on the second medical image, to an identical external apparatus.

9. The control apparatus of claim 1, wherein the communication unit is configured to not transmit error information corresponding to the transmitted medical image, in a case where a medical image which has been transmitted to the first external apparatus is subject to modification, and to transmit the modified medical image to the second external apparatus.

10. The control apparatus of claim 1, wherein the error information associated with the obtained medical image further includes reason information for the error.

11. An X-ray imaging apparatus comprising:
a control apparatus of claim 1; and
an X-ray detector.

12. The X-ray imaging apparatus of claim 11, further comprising an X-ray source.

13. A control system including apparatuses for medical imaging, the control system comprising:
a control unit configured to control a medical imaging unit for detecting an X-ray to obtain a medical image; and
a communication unit configured to transmit the obtained medical image to an external apparatus,
wherein the control unit is configured to associate error information with the obtained medical image, wherein the error information indicates an error in the medical imaging for the obtained medial image,
wherein, in a case where control unit associates the error information with the obtained medical image, the communication unit is configured to transmit the obtained medical image to a first external apparatus which is independent from the control apparatus and is configured to store the obtained medical image associated with the error information, and
wherein, in a case where the control unit does not associate the error information with the obtained medical image, the communication unit is configured to transmit the obtained medical image to a second external apparatus which is independent from the control apparatus and different from the first external apparatus and is configured to store an image to be used for diagnosis.

14. A non-transitory computer-readable medium storing a program including instructions to be executed by a computer to perform a process of medical imaging, the process comprising:
controlling a medical imaging unit for detecting an X-ray to obtain a medical image;
associating, using the computer, in response to an operation input, error information with the obtained medical image, wherein the error information indicates an error in the medical imaging for the obtained medical image;
determining an external unit to which the obtained medical image is to be transmitted, based on whether or not the computer associates the obtained medical image with the error information; and
controlling a communication unit to transmit the obtained medical image to an external apparatus,
wherein, in a case where the computer associates the error information with the obtained medical image, the communication unit is configured to transmit the obtained medical image to a first external apparatus which is independent from the computer and is configured to store the obtained medical image associated with the error information, and
wherein, in a case where the computer does not associate the error information with the obtained medical image, the communication unit is configured to transmit the medical image to a second external apparatus which is independent from the computer and different from the first external apparatus and is configured to store an image to be used for diagnosis.

* * * * *